United States Patent [19]

Farmer et al.

[11] Patent Number: 4,911,929
[45] Date of Patent: Mar. 27, 1990

[54] BLOOD SUBSTITUTE COMPRISING LIPOSOME-ENCAPSULATED HEMOGLOBIN

[75] Inventors: Martha C. Farmer, Washington, D.C.; Richard L. Beissinger, Oak Park, Ill.

[73] Assignee: The United States of America as represented by the Secretary of the Navy, Washington, D.C.

[21] Appl. No.: 192,045

[22] Filed: May 9, 1988

Related U.S. Application Data

[62] Division of Ser. No. 901,710, Aug. 29, 1986, Pat. No. 4,776,991.

[51] Int. Cl.$^4$ .................. A61K 37/22; A61K 9/42; B01J 13/02
[52] U.S. Cl. .................. 424/450; 428/402.2; 436/829; 514/6; 514/832; 514/833
[58] Field of Search .................. 364/4.1, 4.3, 4.6; 428/402.2; 424/450; 436/829; 514/6, 832, 833

[56] References Cited

U.S. PATENT DOCUMENTS

| | | | |
|---|---|---|---|
| 4,016,100 | 4/1977 | Suzuki et al. | 424/450 X |
| 4,133,874 | 1/1979 | Miller et al. | 424/450 |
| 4,425,334 | 1/1984 | Hunt et al. | 436/829 X |
| 4,448,765 | 5/1984 | Ash et al. | 424/450 |
| 4,483,873 | 11/1984 | Ohashi et al. | 514/788 X |
| 4,501,728 | 2/1985 | Geho et al. | 424/450 |
| 4,515,736 | 5/1985 | Deamer et al. | 264/4.3 |
| 4,532,130 | 7/1985 | Djordjevich et al. | 514/6 X |
| 4,649,151 | 3/1987 | Dougherty et al. | 514/410 |
| 4,675,310 | 6/1987 | Chapman et al. | 514/6 |
| 4,776,991 | 10/1988 | Farmer et al. | 264/4.3 |

FOREIGN PATENT DOCUMENTS

83/00089  1/1983  PCT Int'l Appl.

OTHER PUBLICATIONS

Hunt et al., "Synthesis and Evaluation of a Prototypal Artificial Red Cell", vol. 230, pp. 1165-1168, Dec. 6, 1985.

Gaber et al., "Encapsulation of Hemoglobin in Phospholipid Vesicles", vol. 153, #2, pp. 285-288, Mar. 1983.

*Primary Examiner*—Richard D. Lovering
*Attorney, Agent, or Firm*—Thomas E. McDonnell; A. David Spevack

[57] ABSTRACT

Sterile liposome-encapsulated hemoglobin having an oxygen carrying capacity of 20 vol/%, a half life of 15-20 hours as measured in mice, with the liposome made from chloroform, HSPC, cholesterol, negatively charged DMPG and alpha-tocopherol.

7 Claims, 6 Drawing Sheets

BLOOD SUBSTITUTE COMPRISING LIPOSOME-ENCAPSULATED HEMOGLOBIN

This application is a division of U.S. patent application Ser. No. 901,710 filed Aug. 29, 1986, which is now U.S. Pat. No. 4,776,991.

SPECIFICATION

1. Field of the Invention

This invention relates to blood substitutes, and methods for their preparation. More particularly, it relates to a novel composition which can be administered to human patients as a blood substitute by transfusion.

2. Background of the Invention

It is a well known and well documented fact that the demand for blood supplies for administration to patients undergoing surgery and other emergency medical procedures has increased very rapidly over the past 30 years or so. The demand often exceeds the supplies available from human donors. Even larger volumes of blood would be used if it were readily available. Elective surgery is often postponed because of shortages of blood. Sophisticated medical techniques such as organ transplants continue to become more successful and more common so that the amounts of blood required continues to increase. Extracorporeal techniques require large quantities of blood, mostly for temporary use. There is therefore a need to develop blood supplies which are available. The need exists not only in areas where advanced medical techniques are practiced, but also in underdeveloped areas of the world where expensive facilities for blood banking are not available.

The use of whole blood for transfusions has several known disadvantages. To avoid an antigenic reaction, the recipient's blood must be accurately typed and matched to compatible blood from a donor, necessitating excess stored units and the loss of valuable time in emergency situations. It can only be transfused in hospitals rather than emergency vehicles at the site of a trauma. Currently, whole blood can be stored at 4° C. for no longer than three weeks before a considerable fraction of the red blood cells become osmotically fragile and non-viable. Frozen cells must be washed free of glycerol, which is expensive and time consuming, and these cells are also somewhat osmotically fragile. Also, the risk of transmitting disease by transfused blood is quite high, most notably non A/non B hepatitis, parasites and AIDS.

A blood substitute capable of more than just fluid replacement has been actively sought by researchers around the world for some 15 years and in Japan perfluorinated hydrocarbons are currently being used in this context. Oxygen is very soluble in these compounds, but ambient oxygen is not sufficient to satisfactorily improve the oxygen carrying capacity, necessitating an oxygen tent which is unsuitable for many emergency situations, especially combat emergencies. It has also been declared unsuitable for clinical trials in this country due to other complications. To avoid these difficulties, hemoglobin has been suggested and used as a blood substitute.

Use of hemoglobin solutions has the advantage as compared with use of whole blood, that blood typing would not have to be undertaken. Such solutions therefore could be given to a patient in an emergency without taking the time to type and cross-match the blood. Blood types are genetically determined and are the result of specific antigens present on the surface of the red blood cells (RBCs). The hemoglobin within the cells does not exhibit a blood type once separated from the cell membranes or stroma. Moreover, hemoglobin is a much easier material to store than whole blood, and does not deteriorate as quickly. Stocks of blood have to be discarded after a relatively short period of time. Hemoglobin can be isolated from blood and frozen so that it can be stored for a much longer period of time. Use of hemoglobin solutions instead of whole blood thus would have significant advantages, and would tend to alleviate problems of lack of supply of whole blood, particularly lack of supply of blood of specific types.

However, hemoglobin is rapidly excreted by the kidneys into the urine and some resultant renal dysfunction has been observed. Frequent massive transfusions of hemoglobin solution, if employed to balance the high rate of excretion, would certainly pose a hazard to patients with pre-existing renal disease. It has been reported that the circulation half-life, defined as the time for disappearance of half of the hemoglobin administered in a solution by transfusion, is only one and one-half hours in monkeys.

Therefore, there have been efforts to encapsulate stroma-free hemoglobin in an antigen-free encapsulant which would allow for adequate oxygenation of the hemoglobin, prevent renal excretion of the hemoglobin, and insure ample circulation half-time of the hemoglobin. The principal difficulty with these efforts heretofore has been the inability for preparing enough product with sufficient $O_2$ carrying capacity for large-scale animal testing.

The present synthetic red cell concept actually dates from 1964 when T. M. S. Chang first encapsulated hemoglobin in collodion or nylon membranes (T. M. S. Chang, *Science* 146:524 (1964)). Crosslinked hemoglobin used as a membrane (T. A. Davis, W. J. Asher, and H. W. Wallace, *Appl. Biochem. Biotech.* 10:123 (1984)), (M. C. Levy, P. Rambourg, J. Levy, and G. Potron, *J. Pharmaceut. Sci.* 71:759 (1982)) and other polymeric membranes (M. Arakawa, A. Kato, and T. Kondo, *Appl. Biochem. Biotech.* 10:143 (1984)), J. A. Hayward, D. M. Levine, L. Neufeld, S. R. Simon, D. S. Johnston, and D. Chapman, *FEBS Letters* 187:261 (1985)), M. Ndong-Hkoume, P. Labrude, J. C. Humbert, B. Teisseire, and C. Vigneron, *Annales Pharmaceut. Franc* 39:247 (1981)), now are being investigated as well. Oxidation of the hemoglobin has been a complication with these methods so far, though they all hold promise. Another version is the incorporation of iron-porphyrin derivatives in the membrane of liposomes rather than in the globin protein, such that the "cell" membrane rather than the aqueous interior serves as the $O_2$ carrying site (E. Tsuchida, H. Nishide, M. Yuasa, and M. Sekine, *Bull. Chem. Soc. Japan,* 57:776 (1984)).

U.S. Pat. No. 4,133,874 to Miller et al., incorporated herein by reference, describes lipid-encapsulated hemoglobin cells. One embodiment contains lecithin ex ovo, cholesterol, and phosphatidic acid in a 15:10:1 molar ratio. Another embodiment contains lecithin ex ovo, cholesterol and phosphatidylserine in a 9:7:1 ratio. The method described by Miller et al. has not been amenable to scale up (*Business Week,* 17 June 1985 page 149). Moreover, the sizes of the hemoglobin "cells" obtained were not uniform, ranging from 0.1 to 10 microns, potentially inhibiting proper circulation. In addition, the vigorous stirring or ultrasonic energy required by Miller et al. tends to result in some damage to the encapsulated hemoglobin. Further, the Miller "cells" lack a well-defined structure and are multilayered. A method described by Gaber et al. for liposome encapsulated hemoglobin, patent application Ser. No. 508,692 (now abandoned), had the advantage of a uniform "cell" size, but depends on successive extrusions through membranous filters which yield a final product of approximately 1 ml/sq. in. of filter. The largest extrusion chambers available are not adequate to produce a batch size of one liter of liposomes by this method as well as high encapsulation efficiency. The method also used synthetic phospholipids which had the advantage of purity, but are excessively expensive. The method of Hunt et al., U.S. Pat. No. 4,425,334 involves six steps in the encapsulation alone and has proven very difficult to scale up (*Science* 230, p. 1165, 1985). All three of the above mentioned methods use different phospholipids, yet the circulation half-life as measured in mice is only about 4-5 hours in each case, substantially less than desirable for a blood replacement.

OBJECTS OF THE INVENTION

It is an object of the present invention to provide a blood substitute or blood extender, for administration to human or animal patients.

It is another object of the present invention to provide such a substitute which is also an oxygen carrier, based upon hemoglobin.

It is a further object of the present invention to provide a blood substitute or extender capable of circulating many hours within the circulatory system of the recipient and having adequate oxygenation characteristics.

It is still another object of the present invention to provide a blood substitute or extender consisting of hemoglobin-containing liposomal vesicles which are of nearly a uniform size, averaging 0.2 microns in diameter, having generally a simple lipid bilayer and which are sterilizable.

It is yet another object of the present invention to provide a process for preparing a blood substitute or blood extender without chemical reaction to modify native hemoglobin.

It is another object of the present invention to provide a blood substitute or blood extender via an aseptic process capable of yielding at least 10 ml/min of sterile product.

It is another object of the present invention to provide a blood substitute or blood extender which has a half-life, as measured in mice, of at least 15 hours.

It is another object of the present invention to provide a method of producing blood substitutes or blood extenders that is a large-batch or continuous flow encapsulation system which can be easily scaled up.

These and other objects of the present invention are accomplished with a method for encapsulating in liposomes at least 7 ml/min of sterile hemoglobin, resulting in a narrow liposomes size distribution, the large liposome being approximately 0.25 microns. Moreover the liposome encapsulated hemoglobin would have an oxygen carrying capacity of at least 20 vol/% (measured on packed liposomes) or roughly half that of peaked red blood cells and would have a half-life of 15-20 hours as measured in mice. This method comprises the steps of isolating sterile hemoglobin from human or bovine red blood cells; mixing, in chloroform, hydrogenated soy phosphatidyl chloline (HSPC; approximate composition is 85% distearoyl phosphatidyl choline, 15% dipalmitoyl phosphatidyl choline), cholesterol, negatively charged dimyristoyl phosphatidyl glycerol (DMPG) and alpha-tocopherol to form a homogenous solution of lipids in a ratio of 5:4:1:0.2; evaporating away the chloroform to form an homogenous film of lipids; adding the sterile hemoglobin to the homogenous film of lipids; dispersing the lipids throughout the hemoglobin by gentle agitation at 35° C. for 45 min. to form multilamellar liposomes with encapsulated hemoglobin; continuing gentle rotary agitation of the lipid and hemoglobin at 4° C. degrees for 10-16 hours (overnight) to increase encapsulation; forcing the liposomes and hemoglobin through a sterilized Microfluidizer TM at a pressure of 2000-3000 psi to induce cavitation and high shear which breaks the multilamellar liposomes and produces large unilamellar liposomes with efficient capture of hemoglobin; recycling the liposomes and hemoglobin through the microfluidizer until a uniform size distribution of liposomes is reached; removing by filtration any unencapsulated hemoglobin; temporarily shrinking the liposomes by hyperosmatic shock with added saline; and sterilizing the liposome encapsulated hemoglobin by pressure filtration through 0.22 micron sterilizing filters.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, herein.

DESCRIPTION OF THE PREFERRED EMBODIMENTS

The lipid formulations that have been used successfully by various investigators for encapsulating hemoglobin are all very similar: roughly equivalent quantities of cholesterol and phosphatidylcholine, with 5 to 10% negatively charged lipid, such as phosphatidic acid, dicetyl phosphate, or dimyristoyl phosphatidyl glycerol (DMPG). For reasons delineated below, a mixture of hydrogenated soy phosphatidylcholine (HSPC) (obtainable, for example, from American Lecithin Co., Atlanta, Ga.) cholesterol, Dimyristoyl phosphatidyl glycerol (DMPG) (obtainable, for example, from Avanti Polar Lipids, Birmingham, Ala.) and alpha tocopherol in a molar ratio of 5:4:1:0.2 is used in the preparation described here. Substitution of the synthetic equivalent of HSPC, distearoyl phosphatidylcholine (DSPC), for HSPC gives similar results. A solution of the lipid in chloroform is dried to form a homogenous film and is hydrated with buffered hemoglobin solution (pH 7.4).

The present method of encapsulation evolved from that of F. Olson, C. A. Hunt, F. C. Szoka, W. J. Vail, and D. Paphadjopoulos, *Biochem, Biophys, Acta* 557:9 (1979) and is fully described in *Methods in Enzymology* (M. C. Farmer and B. P. Gaber, in press (1986)). In essence the lipid/aqueous multi-lamellar vesicle (MLV) dispersion resulting from hydration of the lipid is low-pressure extruded (50–90 psi) through Nucleapore filters of progressively smaller pore size. This causes pinching and shearing of the MLVs and forms large unilamellar vesicles (LUVs). The very effective method involves neither detergents nor solvents nor sonication, all of which tend to denature hemoglobin (B. P. Gaber, P. Yager, J. P. Sheridan, and E. L. Chang, *FEBS Letters* 153:285 (1983)). The dependency on surface area limits the batch size severly, however, and multiple filter changes make sterile production inconvenient. The new method has the same advantages as the original pressure extrusion method, without the disadvantages. The Microfluidizer forces the dispersion at 2000–4000 psi through an interaction chamber which exerts high shear stress on the MLVs. The material is recirculated until a uniform size distribution of LUVs is reached. The average size depends on the lipid composition, the extrusion pressure, and other variables. (See E. Mayhew, R. Lazo. W. J. Vail, J. King, and A. M. Green, *Biochem, Biophys, Acta* 775:169 (1984)). Two liters of dispersion, which can be processed through the Microfluidizer in less than one hour, are sufficient to provide a final liposome suspension roughly equivalent to two units of blood for a 25% capture. The batch size can be greatly increased using an industrial-sized system, for instance, the M-510 large scale Microfluidizer.

Much of the unencapsulated hemoglobin can be separated from the liposome by centrifugation and recycled. The remainder is removed via diafiltration using cold 30 mM phosphate buffer, pH 7.4 and 0.1 micron filters in a tangential-flow filtration device, e.g. the Pellicon (Millipore Corp., Bedford, Mass.), or the smaller laboratory-scale Minitan. For large batches, many square feet of filter can be used in this system to improve the speed of the washing process. When the unencapsulated hemoglobin has been reduced from 25 g % to approximately 5 mg %, the buffer is changed to 30 mM sodium phosphate, 110 mM NaCl, 3 mM KCl, pH 7.4, or adjusted to plasma ion composition when required for infusion using a Krebs bicarbonate solution (P. Jynge, D. J. Hearse, and M. V. Braimbridge, *J. Therac. Cardiovasc. Surg.* 76:698 (1978)).

More specifically, liposome-encapsulated hemoglobin is produced by first isolating stroma-free hemoglobin. The hemoglobin obtained can be from a human source, in which case it would be from outdated red cells, or from a bovine source, in which case it would be fresh. Moreover, the hemoglobin obtained should be sterile, and nearly pyrogen or endotoxin free by the Limulus amoebocyte lysate test. (A pyrogen is considered to be anything that causes a fever in a rabbit). The initial concentration of the hemoglobin which gives the best encapsulation efficiency for the procedure described here is between 20–25 gms/%. The hemoglobin is phosphate buffered at a pH of 7.4 but additional salts are not included at this stage.

Also needed initially is a homogenous film of lipids to which the hemoglobin is added. The homogenous film of lipids is made by first preparing a chloroform solution of HSPC:cholesterol:negatively charged DMPG:alpha-tocopherol in a molar ratio of 5:4:1:0.2, respectively. The HSPC (mostly DSPC) is the principle bilayer-forming component, and it is responsible for the increased $T_{\frac{1}{2}}$ in circulation compared to DMPC. The HSPC is approximately 50% of the total lipid. DMPG is needed to improve encapsulation and is approximately 10% of the total lipid. Cholesterol, approximately 40% of the total lipid, is needed to make liposomes stable—not leaky and not likely to fuse with each other. It also modifies the fluidity of the membrane, making it less fluid when "melted", but more fluid when "solid" (i.e., above and below $T_m$, the melting transition temperature). Alpha tocopherol is approximately 2% of the total lipid and is an antioxidant. If, for example, 500 ml round bottom flasks are used for the mixing, the chloroform is removed with a rotary-evaporator which leaves a homogeneous film of lipid on the walls of the flasks. To remove any remaining chloroform the flasks are then placed under vacuum overnight.

The sterile hemoglobin is added to the container on whose walls the homogenous layer of lipids has dried. For instance, 200 ml of hemoglobin can be added to the 500 ml round bottom flask which contains the homogeneous film of lipid, such that the lipid concentration in the dispersion is 100 mM. The container with the added hemoglobin is then rotated and incubated at between 30° and 37° (preferably 35° C.) until all the lipid is dispersed.

Figure 5:
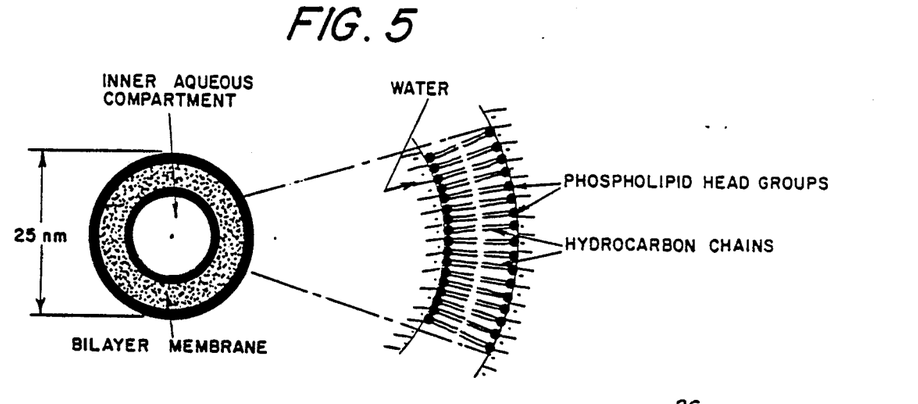
FIG. 5 is a schematic drawing of a cross-section of a large unilamellar vesicle where the aqueous composition is >50%.
Figure 6:
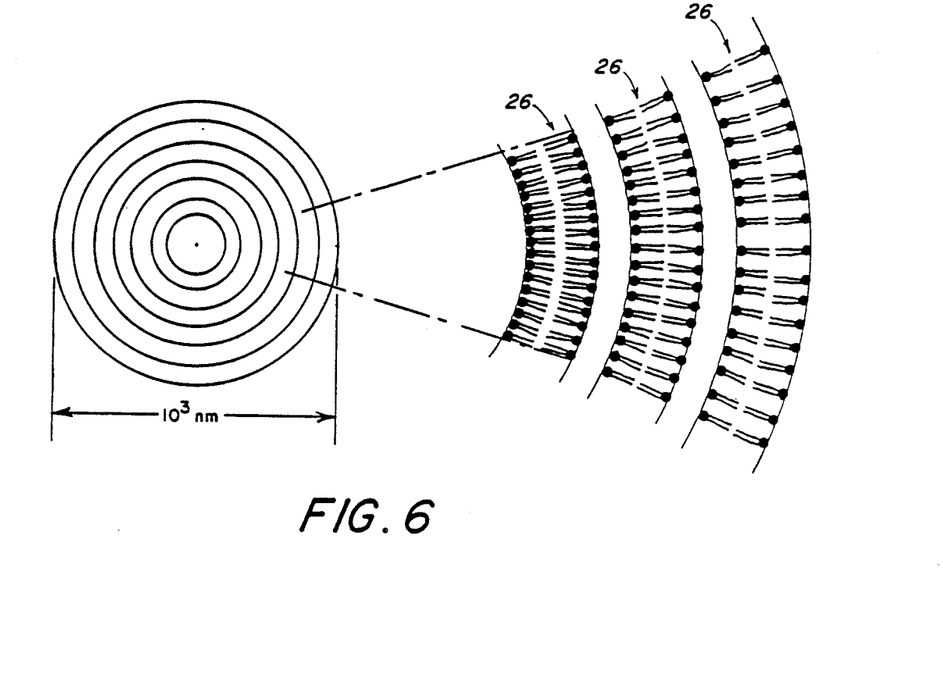
FIG. 6 is a schematic drawing of a cross-section of a multi-lamellar vesicle.

As the dry lipid layer is hydrated by the hemoglobin solution, multilamellar vesicles (MLVs) form (see FIG. 6). This is because of the amphipathic nature of the individual lipids, meaning both hydrophilic and hydrophobic portions co-existing on the same molecule. On distearoyl phosphatidyl, the phosphatidylcholine head group is hydrophilic and the two stearoyl chains (18 carbon saturated fatty acids) are hydrophobic. When the hemoglobin solution is added to the homogenous film of lipids, the hydrophobic tails or stearoyl chains cling together, and pair up with stearoyl chains of other lipids to exclude water. The phosphatidylcholine head group orients towards the water (forming either a micelle (FIG. 2) or a patch of lipid bilayer (FIG. 3). The lipid bilayers form liposomes (FIG. 4) which can have a single bilayer (FIG. 5) or have multiple bilayers or lamellae on the outside but an aqueous space captured inside (FIG. 6). The use of the charged lipid, dimyristoyl phosphatidyl glycerol (DMPG) greatly aids to increase the captured aqueous volume. FIGS. 1–6 will be more fully discussed below.

After the container with the added hemoglobin has been agitated gently at 30°–37° C., the temperature is reduced to approximately 4° C. The hydration process is allowed to continue for 10–14 hours (overnight) to increase encapsulation. (It should be noted that all subsequent steps are carried out at a temperature of between 2 and 6 degrees and preferably 4 degrees.)

The resultant mixture, which now contains mostly MLVs of liposome encapsulated hemoglobin and free unencapsulated hemoglobin, is then forced through a microfluidizer at between 2000 and 3000 PSI in order to break down the MLVs into large unilamellar vesicles (LUVs), simultaneously encapsulating much more hemoglobin in what was the other layers of the MLVs. The outerlayers of the liposomes are removed through the energy intensive operation that occurs in the microfluidizer. The Microfluidizer forces the dispersion at 2000–4000 psi through an interaction chamber maintained at 5°–7° C., which involves a large pressure drop, and consequently a high shear flow. The fluid is divided into two high velocity jets in the thin rectangularly defined micro-channels of the interaction chamber. The fluid streams are directed to impinge with one another at a 180° angle, producing cavitation, and the energy is transferred into breaking down the MLVs to form LUVs. For a typical batch, a flow rate of about 500 ml/min., corresponding to an inlet air pressure of 85 psi is used. The air driven pump in the Microfluidizer M-110 system generates approximately a 5000 psi pressure just upstream of the interaction chamber. At these conditions, fluid flows through the micro-channels with a jet velocity of 10,000 cm/sec at a nominal shear rate of 100,000 $sec^{-1}$. Operated as described, the resultant particle size averages 0.2 microns. See U.S. Pat. No. 4,533,254 to Cook et al. for more detailed information on the principle of operation of the Microfluidizer.

What remains of the mixture at this point is hemoglobin outside as well as inside the LUVs. To remove the remaining unencapsulated hemoglobin, the mixture is passed through a 0.1 micron filter using, for example, a Pellicon TM (Millipore Corp.) tangential flow filtration system. As the hemoglobin outside the LUV is removed, the fluid is replaced with a phosphate buffer at a pH of 7.4 via a constant volume diafiltration.

Figure 11:
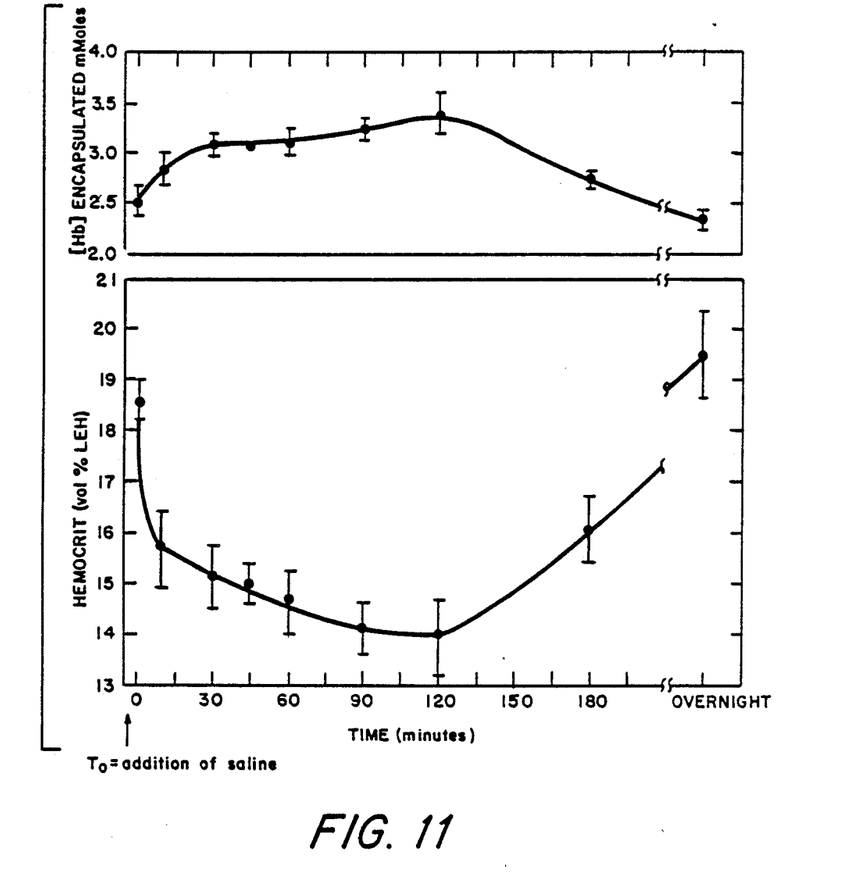
FIG. 11 is a graph of the packed "cell" volume and internal hemoglobin concentration as a function of time following addition of hyperosmotic saline. The liposomes shrink rapidly and can be sterile filtered under pressure before reswelling. The final ion concentrations are appropriate for intravenous infusion.

A final sterilization can then be performed for additional safety, though aseptic technique is used throughout the process and all materials are sterile. This is done upon addition of a hyperosmotic buffered saline solution to the liposome encapsulated hemoglobin causing the individual liposomes to shrink rapidly. During the succeeding 2 hour period, they can be made to pass through a 0.22 micron filter using, for example, the Pellicon TM system (FIG. 11). The final saline solution is adjusted for physiological compatibility of ion composition.

Figure 1:
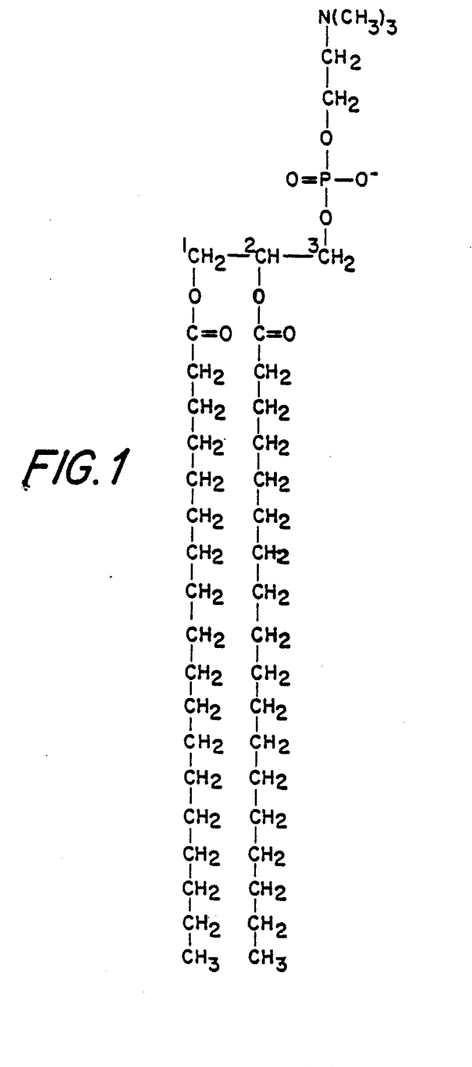
FIG. 1 is a schematic drawing of a distearoyl phosphatidylcholine, the principle component of HSPC.
Figure 2:
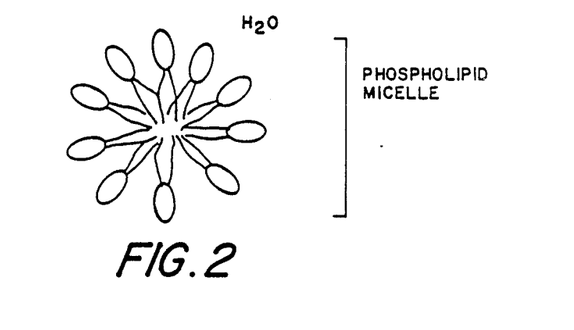
FIG. 2 is a schematic drawing of a cross-section of a phospholipid micelle.
Figure 3:
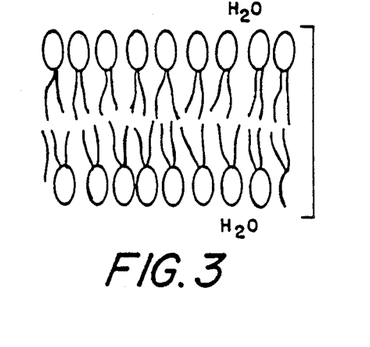
FIG. 3 is a schematic drawing of a cross-section of a phospholipid bilayer.
Figure 4:
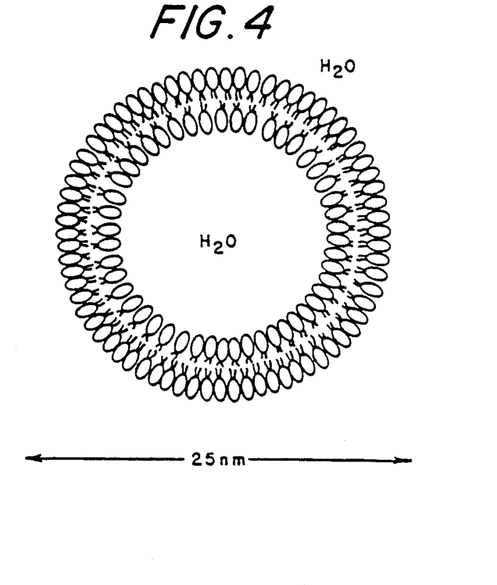
FIG. 4 is a schematic drawing of a cross-section of a small spherical liposome.

Referring now to FIGS. 1–6, FIG. 1 is a chemical representation of distearoyl phosphatidylcholine. Note the 2 hydrocarbon or acyl chains which constitute the hydrophobic tail 12, and the phosphatidylcholine group 16, which is hydrophilic. FIGS. 2 and 3 are schematic drawings of a phospholipid micelle and a phospholipid bilayer seen in cross-section. Phospholipid molecules spontaneously form such structures in water as explained above. FIG. 4 is a schematic cross-sectional view of a "large" unilamellar vesicle (LUV) which may actually range in size between 0.05 microns up to tens of microns. FIG. 5 shows a small unilamellar vesicle (SUV) that is typically smaller than 0.05 microns. FIG. 6 shows a multilamellar vesicle (MLV) usually above 0.8 microns. Note the layers 26 of lipids.

The search for an inexpensive source of phosphatidylcholine for scale-up process development led to investigation of egg and soy lecithins. Egg lecithin has a convenient solid-to-fluid phase transition or melting temperature ($T_m$) for production of liposomes, being very fluid at room temperature. But, egg lecithin results in relatively rapid oxidation of the hemoglobin, in conjunction with the oxidation of the unsaturated bonds in the acyl chains. A slow but steady rate of oxidation is seen even in the presence of alpha tocopherol, a potent antioxidant. (See C. A. Hunt and R. R. Burnette, in: "Advances in Blood Substitute Research," R. B. Bolin, R. P. Geyer, and G. J. Nemo, eds., Alan R. Liss, Inc., New York (1983); and C. A. Hunt, R. R. Burnette, R. D. MacGregor, A. E. Strubbe, D. T. Lau, N. Taylor, and H. Kawada, Science 30:1165 (1985). Distearoyl phosphatidylcholine (DSPC), the major component (85%) of hydrogenated soy lecithin (HSPC), has a high $T_m$ (55° C.) and was assumed unusable for encapsulation of heat labile proteins such as hemoglobin. In previous studies of liposome circulation half-life as a function of phospholipid acyl chain length, however, DSPC (18 carbons) when mixed 1:1 with cholesterol gave a circulation half-life several times that of DMPC (14 carbons) (J. Senior and G. Gregoriadis, Life Sciences 30:2123 (1982)). This desirable quality led us to pursue DSPC despite its high $T_m$. We found that doping DSPC with cholesterol greatly broadens the $T_m$ as measured by calorimetry. (See S. Mabrey-Gaud, in; "Liposomes: From Physical Structure to Therapeutic Applications," C. G. Knight, ed., Elsevier/North Holland, Amsterdam (1981)). Fortunately, hydration of the homogenous lipid mixture of DSPC:cholesterol:DMPG:alpha tocopherol (5:4:1:0.02) with the concentrated hemoglobin solution (20 g %) at 35° C. proved to efficiently encapsulate hemoglobin. HSPC gave similar results to DSPC, both in encapsulation efficiency and in circulation half-life. Alpha-tocopherol has properties similar to cholesterol, but is also a patent antioxidant and helps prevent oxidation of the hemoglobin to methemoglobin during storage, and is therefore added as 2% of total lipid.

Figure 7:
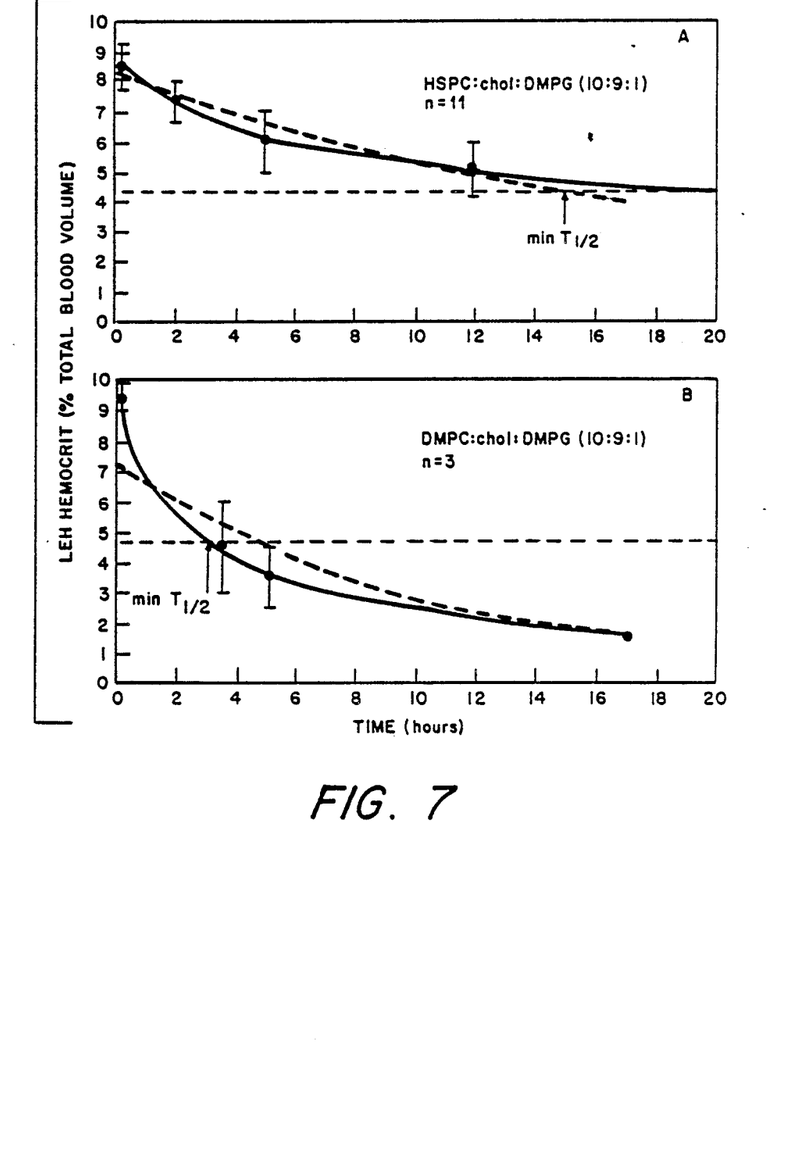
FIG. 7 is a graph of the time required for disappearance from circulation of half of the LEH, the T ½, showing the phospholipid dependence.

Since half-life is dose dependent, a constant dose equivalent to 25% of blood volume was injected into mice for half-life studies. All of the mice survived this procedure, equivalent to a multi-unit transfusion, with no evidence of acute toxicity. FIG. 7 shows the time required for disappearance from circulation of half of the LEH observed at T=0, designated $T_{\frac{1}{2}}$, as estimated from the curves. In the upper graph, a single exponential fit (dotted line) to the four time points (error bars refer to standard deviation n=11 animals at each point) is within the error of the measurement. The fit is much poorer for the lower graph (error bars indicate range of 3 measurements). Uptake of the LEH is via the reticuloendothelial system, a multi-component system for which there is no reason to project a singel kinetic uptake process. Nevertheless it is possible, for the HSPC-based LEH at least, to estimate from the exponential fit a minimum $T_{\frac{1}{2}}$ of 15 hours, and more likely 20 hours. This is a dramatic improvement over the 4 hour minimum seen here with DMPC-based LEH, or the 5.5 hour value seen with egg PC based liposomes as reported by C. A. Hunt, R. R. Burnette, R. D. MacGregor, A. E.

Strubbe, D. T. Lau, N. Taylor, and H. Kawada, *Science* 230:11675 (1985).

Figure 8:
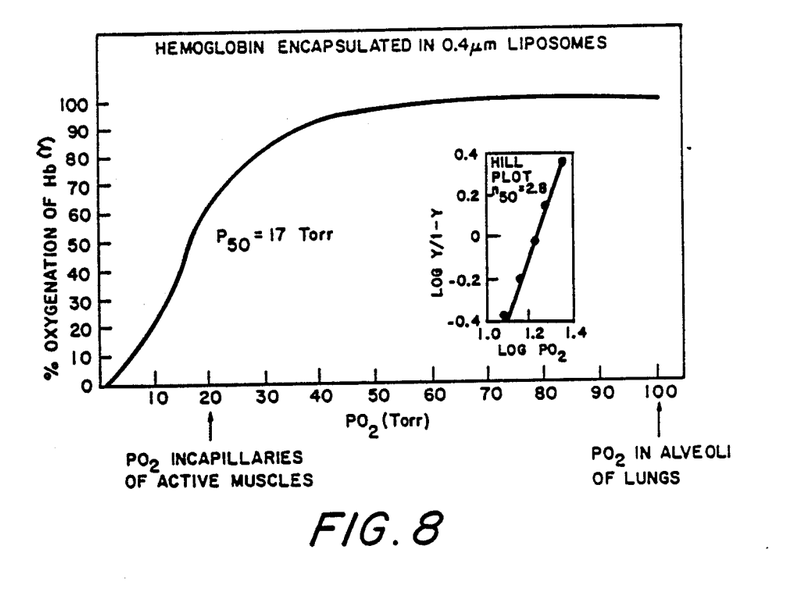
FIG. 8 is a graph of oxygenation measurements of liposome encapsulated hemoglobin in the absence of organic phosphates.
Figure 9:
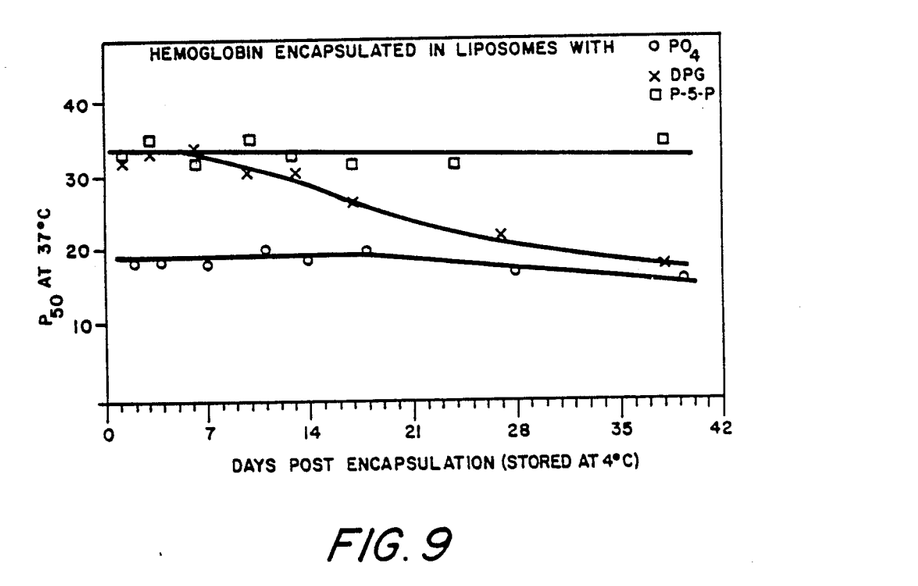
FIG. 9 is a graph of the phosphate and time dependence of the $P_{50}$, the oxygen partial pressure required for 50% oxygenation of the hemoglobin, the standard index of oxygen affinity of hemoglobin. Pyridoxal-5-phosphate (P5P) when co-encapsulated with hemoglobin in liposomes maintains the $P_{50}$; whole 2,3-di-phosphoglycerate (DPG) does not.

FIG. 8 shows the familiar S-shaped oxygen binding curve of hemoglobin indicating that its high cooperativity remains intact after encapsulation. The inset shows the Hill plot, the slope of which, n, is a measure of cooperative oxygen binding, and the value of 2.8 shown here for LEH is the same as for whole blood. The partial pressure of $O_2$ at which the hemoglobin is 50% saturated, defined as the $P_{50}$, can be raised by co-encapsulation of organic phosphates, such as 2.3-diphosphoglycerate (DPG) or pyridoxal-5-phosphate (P-5-P), thus lowering the oxygen affinity to that of fresh RBCs. As can be seen in FIG. 9, P-5-P will actually maintain the high $P_{50}$ of stored LEH for many weeks, much longer than can be achieved with stored RBC's where the intracellular DPG is known to be gradually degraded much as it appears to be here when co-encapsulated in liposomes. An increase in the concentration of P-5-P can further shift the $P_{50}$, resulting in a significantly greater $O_2$ delivery. Such a shift in $P_{50}$ has been shown by Nicolau et al. to be effective in lowering cardiac output of anemic animals (C. Nicolau, B. P. Teisseire, C. Ropass, M-O Vallez, and R. A. Herigault, *Biblthca Haemat*, 51:92 (1985)).

Figure 10:
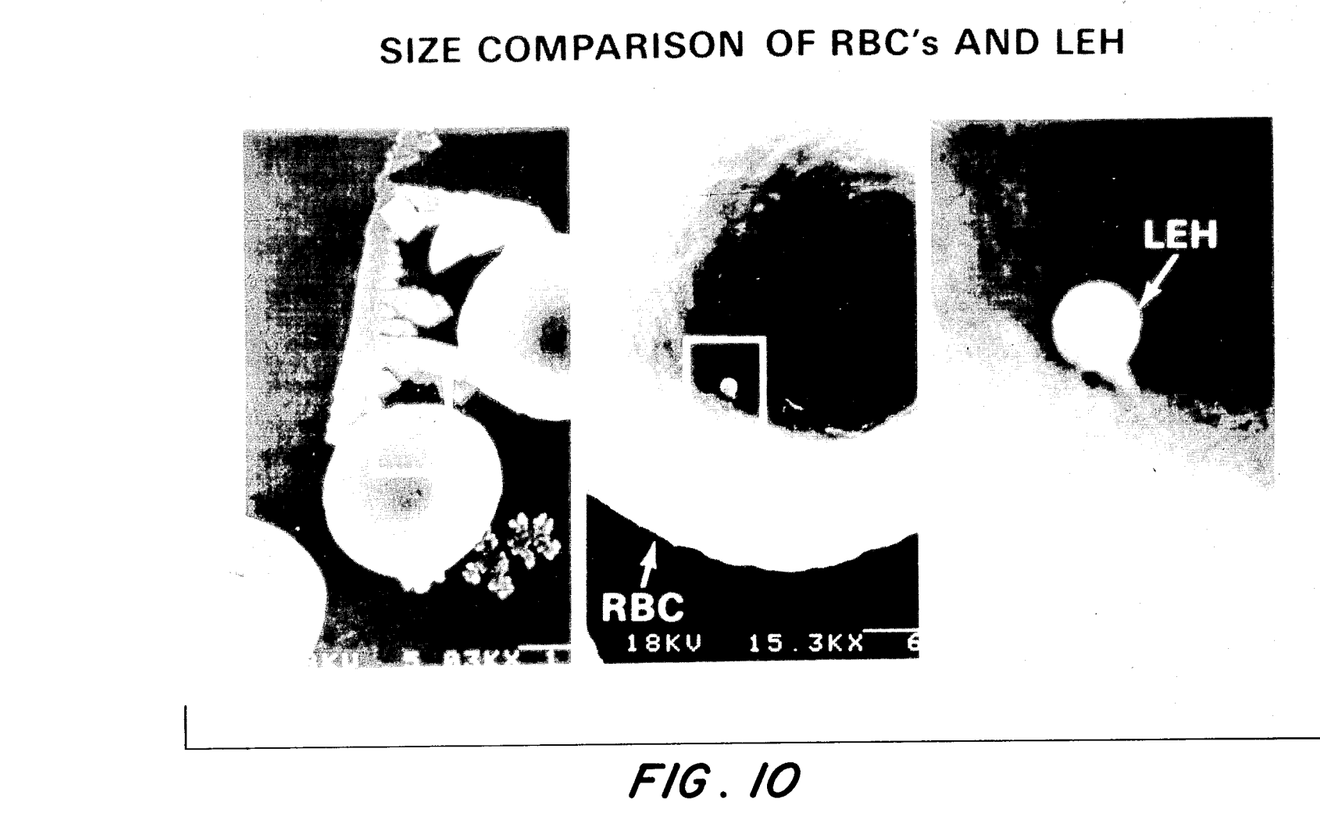
FIG. 10 is scanning electron micrographs of a red blood cell and of a liposome with hemoglobin encapsulated.

The kinetics of $O_2$ binding to LEH have been shown to be much faster than for red blood cells, though slower than for hemoglobin solutions. The rates are, in fact, proportional to the size of the liposomes, being a function of the diffusion distance through the aqueous internal phase (K. Vandegriff and J. Olson, *J. Biol. Chem.* 259:12619 (1984)). The size differential between RBCs and LEH is illustrated in the scanning electron micrograph in FIG. 10. The discoid RBC's average 8×2 microns compared to an average of 0.2 microns for the spherical LEH.

The above results demonstrate that the approach here solves three major problems: extended half-life compared to DMPC and egg PC, extended shelf-life compared to egg PC, and greatly reduced cost. HSPC is approximately three orders of magnitude less expensive than the synthetic DMPC or DSPC.

Furthermore, the Microfluidizer TM yields a stable suspension of 0.2 micron liposomes which encapsulate hemoglobin with a final oxygen carrying capacity of at least 20 vol % for packed LEH, similar to that of the original extrusion method. The concentration of encapsulated hemoglobin depends on the lipid:hemoglobin ratio, and is never more than 70% of the initial hemoglobin concentration in the precursor solution using either method. However, with the Microfluidizer TM, as much as 40% by volume of the total precursor solution can be encapsulated as compared to 10% by the original method.

The advantage offered by 0.2 micron liposomes is that they can be forced through a sterilizing 0.22 micron filter. As mentioned above, this is accomplished by first exposing the liposomes to a hyper-osmotic shock. For example, a volume of phosphate-buffered saline is added to the washed LEH to achieve a final concentration of 30 mM sodium phosphate, 110 mM NaCl, pH 7.4. The liposomes are readily permeable to water and undergo an osmotic shrinkage, decreasing the volume of the liposomes substantially. The permeability of the liposome to the externally applied ions is much lower and it takes many hours for the Donnan equilibrium to be re-established. (Donnan equilibrium refers to the fact that the large impermanent anions inside the liposome, hemoglobin and organic phosphates, cause unequal distributions of diffusable small ions in order to balance the charge.) As ions diffuse in, water follows. At equilibrium there is a balance between osmotic and ionics gradients, and the swelling stops. The time course of shrinking and reswelling, as measured by the packed volume of a suspension of LEH, is shown in FIG. 11. During the 2 hour period following hyperosmotic shock, a dilute liposome suspension can be pressure filtered through the 0.22 micron filters. FIG. 11 shows the change in packed "cell" volume and internal hemoglobin concentration plotted as a function of time following hyperosmotic shock. It can be seen that the liposomes shrink rapidly by some 25% as water diffuses out, and the concentration of hemoglobin consequently rises. The redistribution of ions is relatively slow. Filter sterilization is most efficient during the period immediately following shrinkage.

Obviously numerous (additional) modifications and variations of the present invention are possible in light of the above teachings. It is therefore to be understood that within the scope of the appended claims, the invention may be practiced otherwise as specifically described herein.

What is claimed as new and desired to be secured by Letters Patent of the United States is:

1. A blood substitute having a T ½ of at least 15 hours as measured in mice comprising a fluid medium; and vesicles of a well-defined spherical structure and diameters between 0.15–0.4 microns, said vesicles comprising biologically active hemoglobin and a lipid membrane encapsulating said hemoglobin, said membrane being of at least one lipid bilayer consisting essentially of:

about 30–50 mole percent of cholesterol, about 40–60 mole percent of a saturated phosphatidylcholine with an acyl chain in excess of 14 carbons and about 2 to 10 mole percent of a negatively charged lipid.

2. A blood substitute as described in claim 1 which contains 0 to 10 mole percent lipid soluble antioxidant.

3. A blood substitute as described in claim 2 which includes 0 to 10 percent of alpha tocopherol as the lipid soluble antioxidant.

4. A blood substitute as described in claim 2 which contains sialic acid derivatives of the phosphatidylcoline.

5. A blood substitute as described in claim 2 wherein the phosphatidylcholine is selected from the group consisting of hydrogenated soy phosphatidylcholine, distearoyl phosphatidylcholine and sialic acid derivatives of said phosphatidylcholines and the negatively charged lipid is chosen from the group consisting of phosphatidic acid, dicetyl phosphate and dimyristoyl, dipalmitoyl, or distearoyl-phosphatidyl glycerol.

6. A blood substitute as described in claim 5 wherein the negatively charged lipid is dimyristoyl phosphatidyl glycerol.

7. A blood substitute comprising a fluid medium; and vesicles of a well-defined spherical structure and diameters of between 0.15–0.4 microns, said vesicles comprising stroma-free biologically active hemoglobin and a lipid bilayer encapsulating said hemoglobin, said bilayer consisting essentially of:

hydrogenated soy phosphatidylcholine or distearoyl phosphatidylcholine cholesterol, dimyristoyl phosphatidyl glycerol, and alpha tocopherol in a molar ratio of 5:4:1:0.2.

* * * * *